US011492599B2

(12) United States Patent
Aboussekhra et al.

(10) Patent No.: US 11,492,599 B2
(45) Date of Patent: Nov. 8, 2022

(54) METHOD FOR GENERATING INDUCED PLURIPOTENT STEM CELLS FROM FIBROBLAST CELLS

(71) Applicant: King Faisal Specialist Hospital & Research Centre, Riyadh (SA)

(72) Inventors: Abdelilah Aboussekhra, Riyadh (SA); Hazem Ghebeh, Riyadh (SA); Fauziah Hendrayani, Riyadh (SA)

(73) Assignee: KING FAISAL SPECIALIST HOSPITAL & RESEARCH CENTRE, Riyadh (SA)

( * ) Notice: Subject to any disclaimer, the term of this patent is extended or adjusted under 35 U.S.C. 154(b) by 83 days.

(21) Appl. No.: 15/779,244

(22) PCT Filed: Apr. 18, 2017

(86) PCT No.: PCT/EP2017/059197
§ 371 (c)(1),
(2) Date: May 25, 2018

(87) PCT Pub. No.: WO2018/192641
PCT Pub. Date: Oct. 25, 2018

(65) Prior Publication Data
US 2020/0277576 A1    Sep. 3, 2020

(51) Int. Cl.
*C12N 5/074*    (2010.01)
(52) U.S. Cl.
CPC ........ *C12N 5/0696* (2013.01); *C12N 2500/90* (2013.01); *C12N 2501/2306* (2013.01); *C12N 2506/1307* (2013.01)

(58) Field of Classification Search
CPC .............. C12N 5/0696; C12N 2500/90; C12N 2501/2306; C12N 2506/1307
See application file for complete search history.

(56) References Cited

U.S. PATENT DOCUMENTS

2008/0286243 A1* 11/2008 Kang ...................... A61P 17/14
                                                          424/93.7
2015/0232810 A1*  8/2015 Luo ...................... C12N 5/0696
                                                          424/93.7

FOREIGN PATENT DOCUMENTS

JP    2011160661 A    8/2011
WO    2015003643 A1   1/2015

OTHER PUBLICATIONS

Kim et al. Generation of Human Induced Pluripotent Stem Cells by Direct Delivery of Reprogramming Proteins. Cell Stem Cell. Jun. 5, 2009; 4(6): 472-476. (Year: 2009).*
Sigma-Aldrich. Primary Human Fibroblasts and Growth Media, downloaded from www.sigmaaldrich.com/technical-documents/protocols/biology/fibroblast-cell-culture.printerview.html. p. 1-4. (Year: 2021).*
Stoyanova et al. Early selection of human fibroblast-derived induced pluripotent stem cells. Biotechnology & Biotechnological Equipment, 29:5, 942-948 (Year: 2015).*
Rungarunlert et al. Embryoid body formation from embryonic and induced pluripotent stem cells: Benefits of bioreactors. World J Stem Cells Dec. 31, 2009; 1(1): 11-21 (Year: 2009).*
Yao et al. Animal-cell culture media: History, characteristics, and current issues. Reprod Med Biol. 2017;16:99-117. (Year: 2017).*
Antibiotic-Antimycotic (100x). downloaded from web.archive.org/web/20160214083208/https://www.thermofisher.com/order/catalog/product/15240096. p. 1-2 (Year: 2016).*
Akira, S. et al., "Molecular cloning of APRF, a novel IFN-stimulated gene factor 3 p91-related transcription factor involved in the gp130-mediated signaling pathway." Cell, Apr. 1994, 77 (1): Abstract.
Brady, J. J. et al., "Early role for IL-6 signalling during generation of induced pluripotent stem cells revealed by heterokaryon RNA-Seq." Nature Cell Biology, Sep. 2013, 15: 1-19.
Chen, J. et al., "H3K9 methylation is a barrier during somatic cell reprogramming into iPSCs." Nature Genetics, Jan. 2013, 45 (1): 34-43.
Dethlefsen, C. et al., "The role of intratumoral and systemic IL-6 in breast cancer." Breast Cancer Res. Treat., Apr. 2013, 138 (3): Abstract.
Esteban, M. A. et al., "Vitamin C Enhances the Generation of Mouse and Human Induced Pluripotent Stem Cells." Cell Stem Cell, Jan. 2010, 6: 71-79.
Esteban, M. A., Pei, D., "Vitamin C improves the quality of somatic cell reprogramming." Nature Genetics, Mar. 2012, 44 (4): Abstract.
Gao, S. P. et al., "Mutations in the EGFR kinase domain mediate STAT3 activation via IL-6 production in human lung adenocarcinomas." The Journal of Clinical Investigation, Dec. 2007, 117 (12): 3846-3856.
Knüpfer, H., Preiß, R., "Significance of interleukin-6 (IL-6) in breast cancer (review)." Breast Cancer Research and Treatment, 2007, 102 (2): Abstract.
Li, R. et al., "A Mesenchymal-to-Epithelial Transition Initiates and is Required for the Nuclear Reprogramming of Mouse Fibroblasts." Cell Stem Cell, Jul. 2010, 7: 51-63.
Lieblein, J. C. et al., "STAT3 can be activated through paracrine signaling in breast epithelial cells." BMC Cancer, 2008, 8 (302): 1-14.
Liu, X. et al., "Sequential introduction of reprogramming factors reveals a time-sensitive requirement for individual factors and a sequential EMT-MET mechanism for optimal reprogramming." Nature Cell Biology, May 2013, 15: 1-9.

(Continued)

*Primary Examiner* — Taeyoon Kim
(74) *Attorney, Agent, or Firm* — Saliwanchik, Lloyd & Eisenschenk

(57) ABSTRACT

The present invention relates to methods for generating Induced Pluripotent Stem Cells from fibroblast cells. The invention also relates to appropriate culture media used by the method disclosed; pluripotent stem cells, cultures of the pluripotent stem cells, differentiated cells derived from the culture pluripotent stem cells isolated by the methods disclosed and uses for those cells, e.g. therapeutic uses, such as autologous cell therapy procedures.

16 Claims, 11 Drawing Sheets
Specification includes a Sequence Listing.

(56) References Cited

OTHER PUBLICATIONS

Miyoshi, N. et al., "Reprogramming of Mouse and Human Cells to Pluripotency Using Mature MicroRNAs." Cell Stem Cell, Jun. 2011, 8: 633-638.
Okano, H. et al., "Steps Toward Safe Cell Therapy Using Induced Pluripotent Stem Cells." Circulation Research, Feb. 2013, 112: 523-533.
Raz, R. et al., "Essential role of STAT3 for embryonic stem cell pluripotency." Proc. Natl. Acad. Sci. USA, Cell Biology, Mar. 1999, 96: 2846-2851.
Samavarchi-Tehrani, P. et al., "Functional Genomics Reveals a BMP-Driven Mesenchymal-to-Epithelial Transition in the Initiation of Somatic Cell Reprogramming." Cell Stem Cell, Jul. 2010, 7: 64-77.
Sriuranpong, V. et al., "Epidermal Growth Factor Receptor-independent Constitutive Activation of STAT3 in Head and Neck Squamous Cell Carcinoma is Mediated by the Autocrine/Paracrine Stimulation of the Interleukin 6/gp130 Cytokine System." Cancer Research, Jun. 2003, 63: 2948-2956.
Wang, T. et al., "The Histone Demethylases Jhdm1a/1b Enhance Somatic Cell Reprogramming in a Vitamin-C-Dependent Manner." Cell Stem Cell, Dec. 2011, 9: 575-587.
Yu, J. et al., "Human Induced Pluripotent Stem Cells Free of Vector and Transgene Sequences." Science, May 2009, 324: 1-23.

* cited by examiner

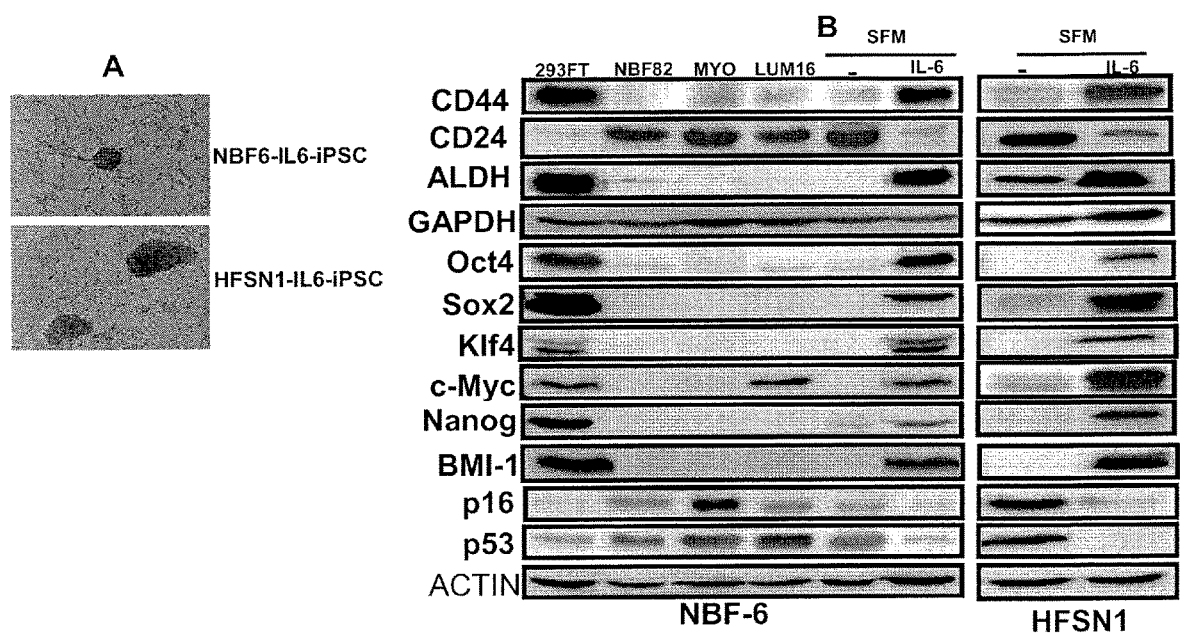
Figure 1: IL-6 induces pluripotency in breast (NBF-6) and skin (HFSN1) human fibroblast cells

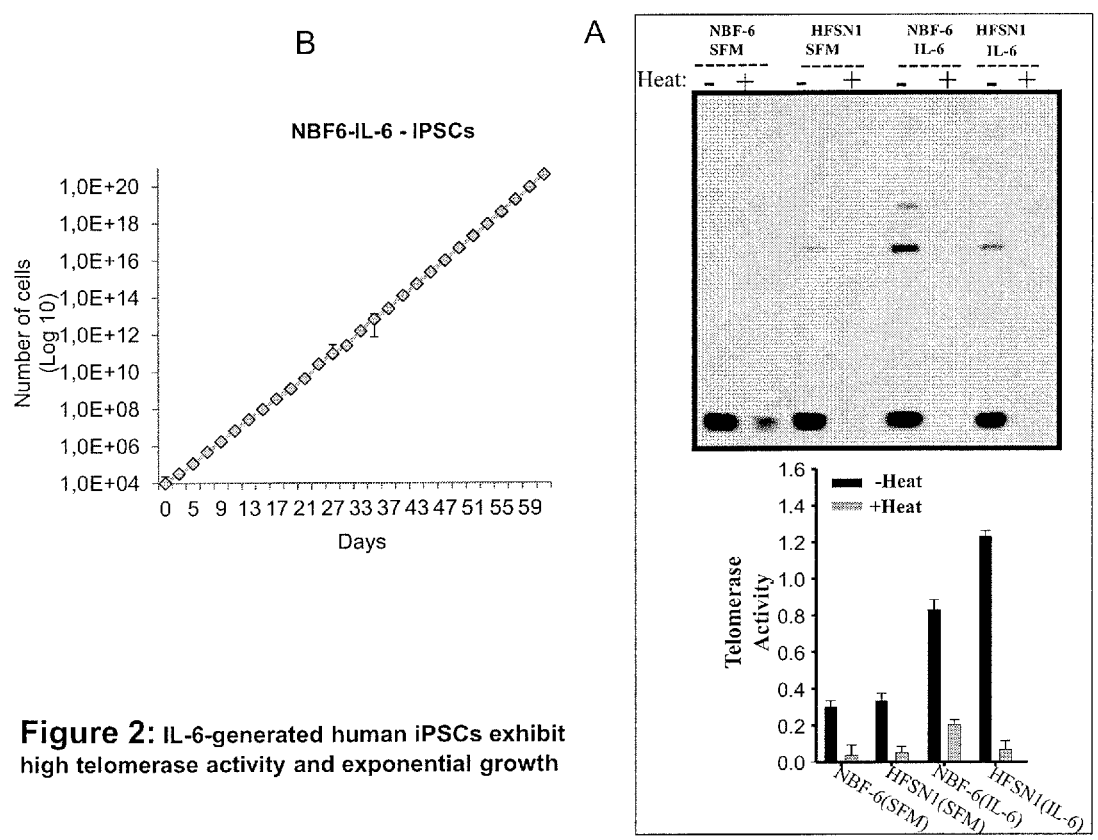
Figure 2: IL-6-generated human iPSCs exhibit high telomerase activity and exponential growth

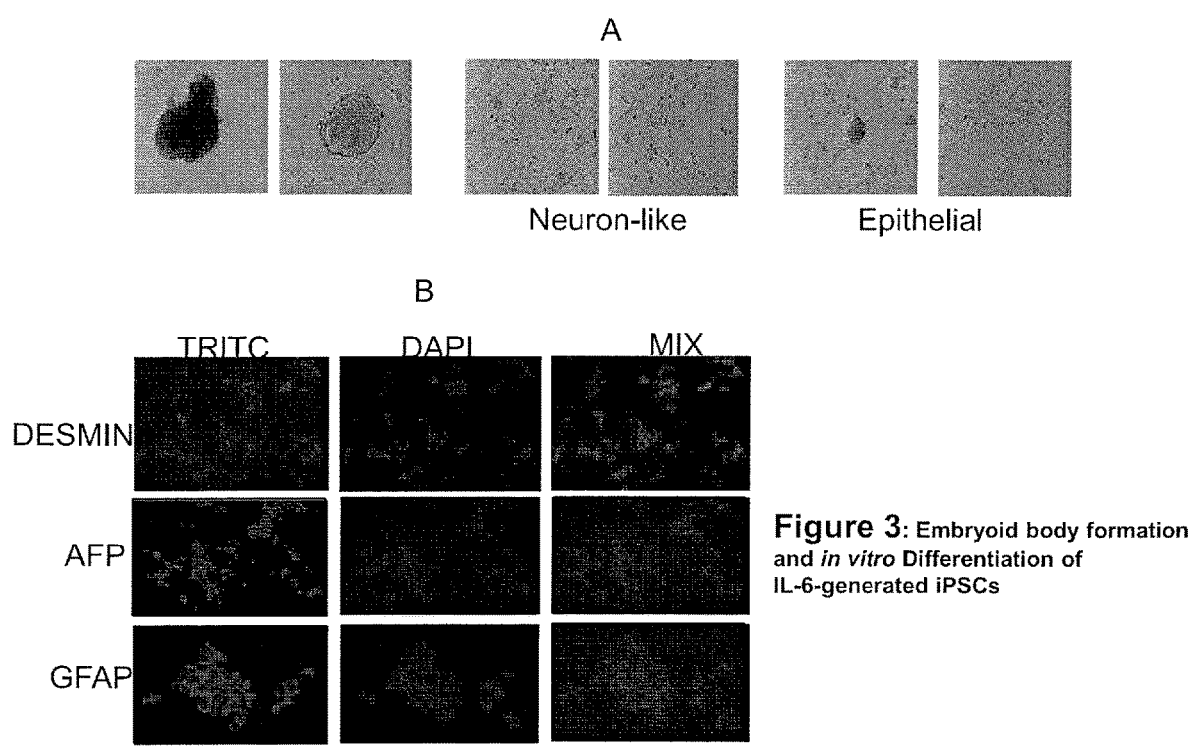
Figure 3: Embryoid body formation and *in vitro* Differentiation of IL-6-generated iPSCs

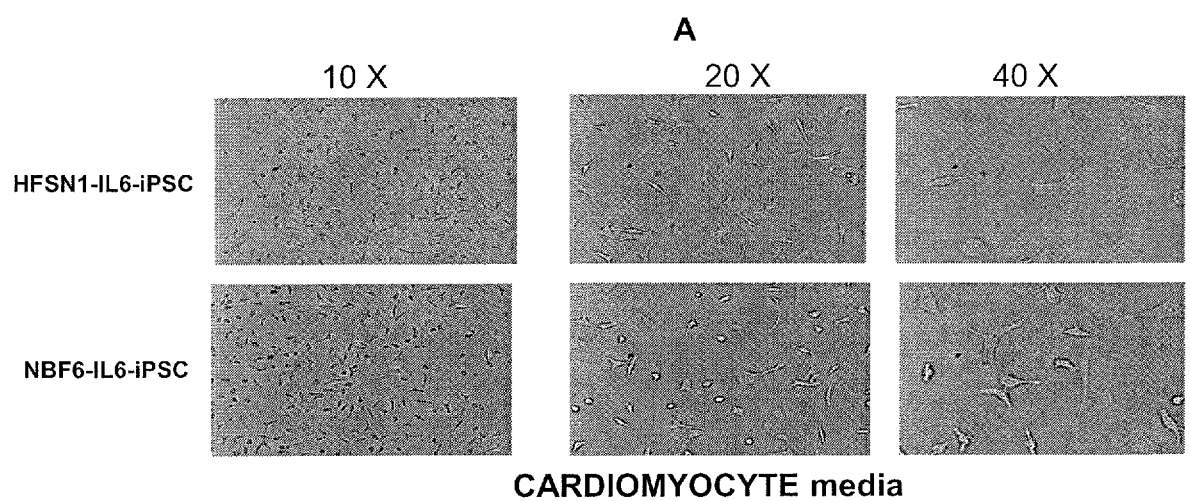
Figure 4: Differentiation and growth in specific culture medium

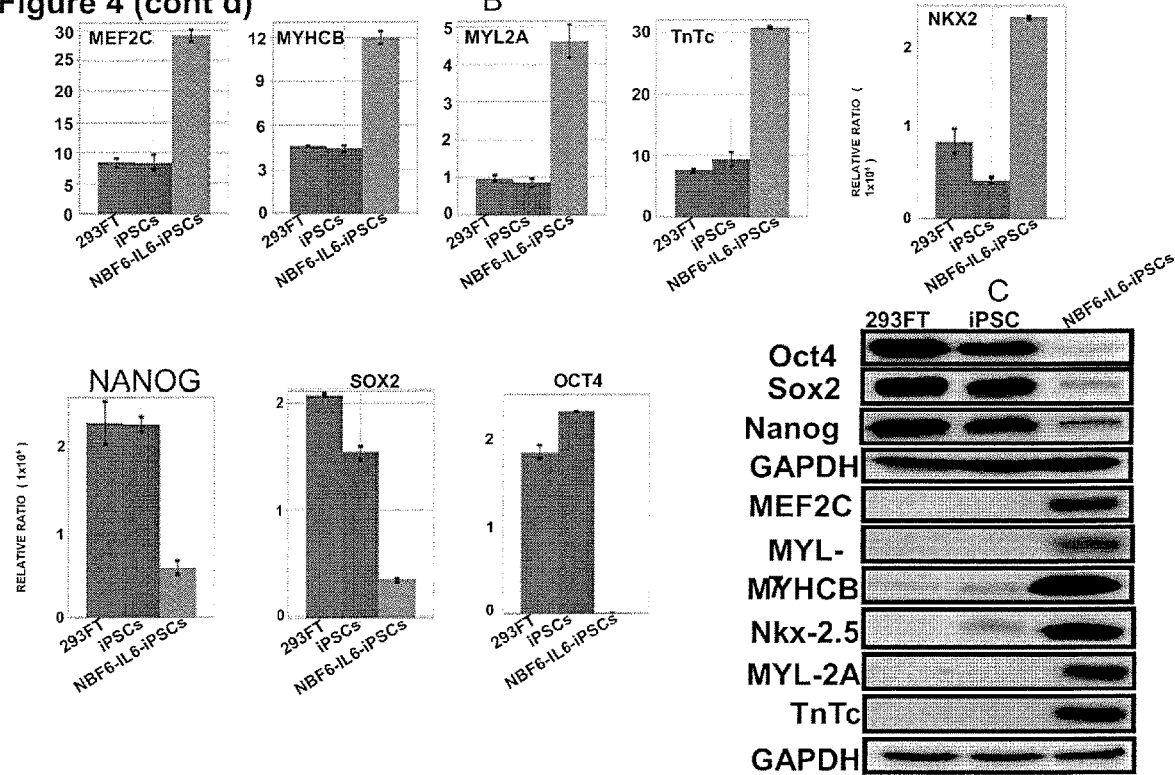

D

Neuronal specific growing medium

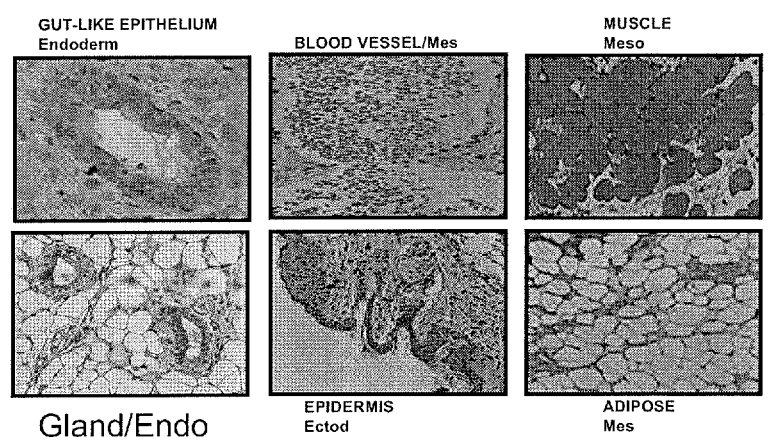
Figure 5: IL-6-generated iPSCs formed teratoma in nude mice

METHOD FOR GENERATING INDUCED PLURIPOTENT STEM CELLS FROM FIBROBLAST CELLS

CROSS REFERENCE TO A RELATED APPLICATION

This application is a National Stage Application of International Application Number PCT/EP2017/059197, filed Apr. 18, 2017.

The Sequence Listing for this application is labeled "SeqList-23May18-ST25.txt", which was created on May 23, 2018, and is 3 KB. The entire content is incorporated herein by reference in its entirety.

TECHNICAL FIELD

The present invention relates to methods for generating Induced Pluripotent Stem Cells from fibroblast cells. The invention also relates to appropriate culture media used by the method disclosed; pluripotent stem cells, cultures of the pluripotent stem cells, differentiated cells derived from the culture pluripotent stem cells isolated by the methods disclosed and uses for those cells, e.g. therapeutic uses, such as autologous cell therapy procedures.

BACKGROUND OF THE INVENTION

Induced Pluripotent Stem Cells (iPSCs) can be obtained from various somatic cells through the ectopic expression of 4 defined factors (KLF4, OCT3/4, SOX2 and c-MYC). This provides an unlimited cell resource, with potential use for regenerative medicine.

Generation of iPSCs without genomic integration of extrinsic genes is highly desirable. To this end, Hou et al. generated iPSCs from mouse somatic cells using a combination of 7 small-molecule compounds. It was also possible to reprogram mouse and human cells to pluripotency by direct transfection of mature microRNAs with no vector-based gene transfer. It was also possible to reprogram mouse and human cells to pluripotency using mature miRNAs (Miyoshi et al., Reprogramming of mouse and human cells to pluripotency using mature microRNAs. Cell stem cell 2011, 8, 633-638). Interestingly, vitamin C has been shown to enhance the generation as well as the quality of iPSCs (Chen et al., H3K9 methylation is a barrier during somatic cell reprogramming into iPSCs. Nat Genet 2013, 45, 34-42; Esteban et al., Vitamin C improves the quality of somatic cell reprogramming. Nat Genet 2012, 44, 366-367; Esteban et al., Vitamin C enhances the generation of mouse and human induced pluripotent stem cells. Cell stem cell 2010, 6, 71-79; Wang et al., The histone demethylases Jhdm1a/1b enhance somatic cell reprogramming in a vitamin-C-dependent manner. Cell stem cell 2011, 9, 575-587).

In a recent study, Brady et al reprogrammed heterokaryons using ectopic expression of only OCT4, KLF4 and Sox2, in addition to IL-6, which replaced the oncogenic function of c-Myc and also augmented reprogramming efficiency (Brady et al., Early role for IL-6 signalling during generation of induced pluripotent stem cells revealed by heterokaryon RNA-Seq. Nat Cell Biol 2013, 15, 1244-1252). Interleukin-6 (IL-6) is among those soluble factors that are secreted from both cancer cells and stromal fibroblasts. IL-6 is a multifunctional cytokine that plays a key role in both innate and acquired immune responses, hematopoiesis, inflammation as well as in the regulation of growth and differentiation of cancer cells (Knupfer et al., Significance of interleukin-6 (IL-6) in breast cancer (review). Breast Cancer Res Treat 2007, 102, 129-135). Importantly, IL-6 is an activator of the signal transducer and activator of transcription 3 (STAT3) in various cancer cells, including breast cancer cell lines (Akira et al., Molecular cloning of APRF, a novel IFN-stimulated gene factor 3 p91-related transcription factor involved in the gp130-mediated signaling pathway. Cell 1994, 77, 63-71; Dethlefsen et al., The role of intratumoral and systemic IL-6 in breast cancer. Breast Cancer Res Treat 2013, 138, 657-664; Gao et al., Mutations in the EGFR kinase domain mediate STAT3 activation via IL-6 production in human lung adenocarcinomas. J Clin Invest 2007, 117, 3846-3856.) STAT3 activation can take place through both autocrine expression of IL-6 and paracrine activation by IL-6 from stroma (Lieblein et al., STAT3 can be activated through paracrine signaling in breast epithelial cells. BMC cancer 2008, 8, 302; Sriuranpong et al., Epidermal growth factor receptor-independent constitutive activation of STAT3 in head and neck squamous cell carcinoma is mediated by the autocrine/paracrine stimulation of the interleukin 6/gp130 cytokine system. Cancer Res 2003, 63, 2948-2956). STAT3 plays also essential role for embryonic stem cell pluripotency (Raz et al., Essential role of STAT3 for embryonic stem cell pluripotency. Proc Natl Acad Sci USA 1999, 96, 2846-2851).

Reprogramming of fibroblast cells is a multistep process, whose initiation entails a mesenchymal-to-epithelial transition (MET) orchestrated by the induction of an epithelial program into cells (Li et al., A mesenchymal-to-epithelial transition initiates and is required for the nuclear reprogramming of mouse fibroblasts. Cell stem cell 2010, 7, 51-63; Liu et al., Sequential introduction of reprogramming factors reveals a time-sensitive requirement for individual factors and a sequential EMT-MET mechanism for optimal reprogramming. Nat Cell Biol 2013, 15, 829-838; Samavarchi-Tehrani et al., Functional genomics reveals a BMP-driven mesenchymal-to-epithelial transition in the initiation of somatic cell reprogramming. Cell stem cell 2010, 7, 64-77). KLF4 induces E-cadherin and other epithelial markers, while SOX2 and OCT4 down-regulate SNAIL1 (Li et al., A mesenchymal-to-epithelial transition initiates and is required for the nuclear reprogramming of mouse fibroblasts. Cell stem cell 2010, 7, 51-63).

However, there are still various problems concerning technically challenging technologies, genetic manipulation and low yield which limit the clinical application.

There is therefore a need for developing further methods for generating Induced Pluripotent Stem Cells (iPSCs).

There is also a need to provide iPSCs, cultures of the iPSCs, differentiated cells, tissues and also organs derived from the cultured iPSCs, for their applicability in tissue engineering and cell therapeutics. This will also help scientists and researchers to gain a better understanding of stem cells, and will ultimately lead to better therapies including autologous cell therapy procedures.

There is also a further need for a source of cells that are transplantable to in vivo tissues/organs in order to replace diseased or damaged tissues/organs.

In the present study we present an efficient and vector-free method for generating iPSCs from fibroblast cells.

SUMMARY OF THE INVENTION

In one aspect, the present invention relates to
a method for generating induced pluripotent stem cells (iPSCs) comprising the steps:

a) providing isolated fibroblast cells;

b) growing cells in fibroblast growing medium (FGM), and then treating the fibroblasts in a serum-free medium (SFM) containing interleukin-6 (IL-6); and then growing the thus treated fibroblasts in fibroblast growth medium again, preferably until confluency;

c) performing 1-5, preferably 2-3 cycles of freezing/thawing the cells, and then growing the cells until the formation of cellular floating aggregates;

d) transferring the cells to a growth medium for induced pluripotent stem cells (iPSCs) and growing the cells further until the formation of colonies and expanding further such colonies on feeder cells to result in induced pluripotent stem cells (iPSCs).

In one embodiment, the method according to the present invention further comprises the step:

e) characterizing molecular and cellular characteristics of the formed iPSCs.

In one embodiment, the serum-free medium (SFM) for the treatment of fibroblast cells with IL-6 has a maximum serum content of 0%-1% (vol/vol) serum, preferably ≤0.2% (vol/vol) serum, preferably about 0.2% (vol/vol) serum, wherein the serum is more preferably fetal bovine serum (FBS). In one embodiment of step b) before subsequent treatment with IL-6, the fibroblast cells are grown in fibroblast growth medium until they reach approximately 70%-80% confluency.

In one embodiment, the treatment of step b) lasts for 2-100 hours, preferably in the range of from 12 hours to 72 hours, more preferably in the range of from 12 hours to 48 hours, even more preferably in the range of from 12 hours to 36 hours, even more preferably in the range of from 12 hours to 30 hours, even more preferably in the range of from 20 hours to 28 hours, even more preferably 24 hours.

In one embodiment, the serum-free medium (SFM) in step b) comprises a 1:1-mixture (vol/vol) of M199 medium and F12 medium supplemented with 0%-1% (vol/vol) serum, preferably ≤0.2% (vol/vol) serum, preferably fetal bovine serum (FBS), preferably about 0.2% (vol/vol) FBS, and supplemented with 0.1%-2% (vol/vol) of an antibiotic-antimycotic solution, said antibiotic-antimycotic solution comprising 10000 untils/ml penicillin, 10000 μg/ml streptomycin and 25 μg/ml amphotericin B, preferably 1% of said antibiotic-antimycotic solution, and the fibroblast growth medium in step b) comprises a 1:1-mixture (vol/vol) of M199 medium and F12 medium supplemented with 1%-20% (vol/vol) serum, preferably 10%-20% (vol/vol) serum, preferably 20% (vol/vol) serum, more preferably fetal bovine serum (FBS), and further being supplemented with 0.1%-2% (vol/vol) of antibiotic-antimycotic solution, said antibiotic-antimycotic solution comprising 10000 units/ml penicillin, 10000 μg/ml streptomycin and 25 μg/ml amphotericin B, preferably 1% of said antibiotic-antimycotic solution.

In one embodiment, said interleukin-6 is human interleukin-6, wherein, preferably, said interleukin is recombinant human interleukin-6, preferably having the amino acid sequence

```
                                          (SEQ ID NO: 1)
MNSFSTSAFG PVAFSLGLLL VLPAAFPAPV PPGEDSKDVA

APHRQPLTSS ERIDKQIRYI LDGISALRKE TCNKSNMCES

SKEALAENNL NLPKMAEKDG CFQSGFNEET CLVKIITGLL
```

-continued
```
EFEVYLEYLQ NRFESSEEQA RAVQMSTKVL IQFLQKKAKN

LDAITTPDPT TNASLLTKLQ AQNQWLQDMT THLILRSFKE

FLQSSLRALR QM.
```

In one embodiment, said interleukin-6 is used in step b) in the serum-free medium at a concentration in the range of from 1 ng/ml to 100 ng/ml, preferably 10 ng/ml to 50 ng/ml, more preferably 20 ng/ml to 40 ng/ml, even more preferably about 35 ng/ml.

In one embodiment, the growing of said cells in step d) occurs in an environment that favors suspension cell culture, e.g. low attachment plates.

In one embodiment, the induced pluripotent stem cells are produced by the performance of step a)-d) and are characterized by higher expression of one or several, preferably all of the following: CD44, ALDH, Oct3/4, Sox2, KLF4, c-Myc, Nanog, BMI-1, and reduced or absence of expression of CD24 as well as p16 and p53, in comparison to cells of the same type, i.e. fibroblasts not having undergone the treatment.

In one embodiment, the method according to the present invention further comprises the step of isolating said induced pluripotent stem cells, preferably by means of a pipetting device, preferably under the microscope.

In one embodiment, the fibroblast cells in step a) are mammalian cells, preferably from Primates, more preferably from humans;

or they are rodent cells, more preferably from mouse.

In one embodiment, the method for generating induced pluripotent stem cells (iPSCs) according to the present invention is an in-vitro method.

In one embodiment, said method is a vector-free method.

In one embodiment, said method does not involve an ectopic expression of genes, e.g. an ectopic expression of KLF4, OCT3/4, SOX2 and/or c-MYC.

In one embodiment, said method does not involve the treatment of cells with any interleukin other than interleukin-6 and also not any treatment with vitamin C and also not any transfection of microRNA into said cells.

"Treatment", as used in this context, is meant to refer to a deliberate and intended exposure of cells to an interleukin-containing medium, wherein such interleukin has been specifically added to the medium in which the cells are cultured or to which the cells are exposed.

In a further aspect the present invention relates to an induced pluripotent stem cell or a culture of induced pluripotent stem cells generated by the method for generating induced pluripotent stem cells (iPSCs) according to the present invention.

In a further aspect the present invention relates to a differentiated cell derived from an induced pluripotent stem cell or a culture thereof according to the present invention, or a tissue or organ of such differentiated cells.

In a further aspect the present invention relates to an induced pluripotent stem cell or culture thereof according to the present invention for use in a method of tissue engineering, transplantation, tissue reconstruction, cell therapy procedures, in particular autologous cell therapy procedures, surgical procedures, cosmetic procedures, wherein said use comprises the administration of such induced pluripotent stem cell or differentiated cells derived therefrom to a patient in need thereof.

In a further aspect the present invention relates to the use of a pluripotent stem cell according to the present invention for the manufacture of a medicament for a method of tissue engineering, transplantation, tissue reconstruction, cell therapy procedures, in particular autologous cell therapy procedures, surgery or cosmetic treatment.

In a further aspect the present invention relates to a method of tissue engineering, transplantation, tissue reconstruction, cell therapy procedures, in particular autologous cell therapy procedures, surgery or cosmetic treatment, comprising the steps:

generating pluripotent stem cells according to the present invention by a method according to the present invention, and differentiating them into a desired cell type,
applying/administering such differentiated cells to a patient in need thereof.

In one embodiment, such method is a cosmetic method, or in another embodiment, it is a medical treatment method.

The term "treatment", as used herein in this context, refers to an exposure of said fibroblasts to interleukin-6. In one embodiment such treatment occurs by adding interleukin-6 to the medium in which said fibroblasts are cultured or to which the cells are exposed.

In one embodiment, said fibroblast cells from which the iPSCs are generated are selected from breast fibroblasts, skin fibroblasts, mouse fibroblasts, in particular mouse embryonic fibroblasts.

A "freezing/thawing cycle", as used herein, refers to a procedure wherein the cells are frozen in liquid nitrogen in a suitable freezing medium and subsequently thawed again. Such suitable freezing media are known to a person skilled in the art and are widely commercially available. They are typically characterized by the presence of a suitable cryoprotectant, e.g. DMSO, e.g. 10% DMSO. An example is ThermoFisher's "Recovery®" cell culture freezing medium, cat no. 12648-010 or 12648010. After freezing, the cells are thawed again, typically in an environment at a temperature of >30° C., e.g. 37° C. This could be a water bath, an incubator, a heating block or other suitable thermostatting device. In one embodiment, the cells are grown again between two freezing/thawing cycles; in one embodiment, such growth is done in a fibroblast growth medium (FGM); in one embodiment, the cells are grown until confluency between two freezing/thawing cycles.

In one embodiment, the method for generating induced pluripotent stem cells is a vector-free method. A "vector-free" method is a method where no vector or other instrument for gene transfer is used.

In one embodiment, said method does not involve an ectopic expression of genes, e.g. an ectopic expression of KLF4, OCT3/4, SOX2 and/or c-MYC. "Ectopic expression" as used herein, refers to the expression of a gene or several genes in a cell or tissue where such gene(s) is(are) not normally expressed or to the expression of one or several genes at a point in the cell cycle or in an organism's development when such gene(s) is(are) not normally expressed.

In one embodiment, the method according to the present invention does not involve the treatment of the cells with any interleukin other than interleukin-6 and also not any treatment with vitamin C and also not any transfection of microRNA into said cells. As used herein in this context of vitamin C, the term "treatment" refers to the deliberate and intended addition or administration of vitamin C on its own as sole compound to said cells.

In one embodiment, the medium for the treatment of fibroblast cells with IL-6 is a serum-free medium (SFM) containing interleukin-6 (IL-6).

In one embodiment, the serum-free medium (SFM) that is used for treating fibroblasts is a medium that has, at a maximum, 0%-1% (vol/vol) serum, preferably ≤0.2% (vol/vol) serum, preferably fetal bovine serum (FBS), preferably about 0.2% (vol/vol) FBS. In one embodiment, said medium for the treatment of fibroblasts with IL-6 comprises or is a 1:1 mixture (vol/vol) of M199 medium and F12 medium, supplemented with 0%-1% (vol/vol) serum, preferably ≤0.2% (vol/vol) serum, preferably fetal bovine serum (FBS), preferably about 0.2% (vol/vol) FBS, and supplemented with 0.1%-2% (vol/vol) of an antibiotic-antimycotic solution, said antibiotic/antimycotic solution comprising 10000 units/ml penicillin, 10000 µg/ml streptomycin and 25 µg/ml amphotericin B, preferably 1% of said antibiotic-antimycotic solution. In an embodiment, wherein such SFM is used for treating fibroblasts with interleukin-6, the serum-free medium (SFM) additionally contains interleukin-6 (IL-6).

Growth media for induced pluripotent stem cells (iPSCs) are known to the person skilled in the art and are commercially available. For example, a wide range of such growth media are available from various manufacturers, such as Thermo Fisher of Gibco. One example of such media is a KnockOut DMEM CTS®.

In one embodiment, in step d), the iPSC growth medium has the composition listed in table 1:

TABLE 1

| Reagents For 100 mL | Stock.Conc | Catalog No (Gibco) | Final.Conc |
|---|---|---|---|
| KnockOut DMEM 82.75 mL | — | A12861 | 1X |
| KnockOut SR 15 mL | | 12618 | 15% |
| GlutaMax 1 mL | 200 mM | A12860 | 2 mM |
| NEAA 1 mL | 10 mM | 11140 | 0.1 mM |
| bFGF 80 ul | 10 ug/mL | 13256 | 8 ng/mL |
| 2-Mercaptoethanol 182 uL | 55 mM | 21985 | 0.1 mM |

In one embodiment, said interleukin-6 is human interleukin-6, wherein, preferably, said interleukin-6 is recombinant human interleukin-6, more preferably having the amino acid sequence

```
                                        (SEQ ID NO: 1)
MNSFSTSAFG PVAFSLGLLL VLPAAFPAPV PPGEDSKDVA

APHRQPLTSS ERIDKQIRYI LDGISALRKE TCNKSNMCES

SKEALAENNL NLPKMAEKDG CFQSGFNEET CLVKIITGLL

EFEVYLEYLQ NRFESSEEQA RAVQMSTKVL IQFLQKKAKN

LDAITTPDPT TNASLLTKLQ AQNQWLQDMT THLILRSFKE

FLQSSLRALR QM.
```

Human IL-6 Recombinant protein is commercially available from a variety of sources, e.g. the product hBA-184 is a recombinant human interleukin available from SantaCruzBiotechnology, Inc.

In one embodiment, for treating the fibroblasts, said interleukin-6 is used in step b) at a concentration in the range of from 1 ng/ml to 100 ng/ml, preferably, 10 ng/ml to 50 ng/ml, more preferably, 20 ng/ml to 40 ng/ml, even more preferably about 35 ng/ml.

In one embodiment, the growing of said cells in step d) occurs in an environment that favors suspension cell culture, e.g. low attachment plates or dishes.

In one embodiment, the iPSCs form embryoid bodies and such formed embryoid bodies have a size in the range of from 50 to 300 microns.

In one embodiment, the induced pluripotent stem cells are produced by the performance of step a-d) and are characterized by an increase of expression or overexpression of one or several, preferably all of the following iPSC markers: CD44, ALDH, Oct3/4, Sox2, Klf4, c-Myc, Nanog, BMI-1; and a lower expression or absence of expression of CD24 as well as p16 and p53. in comparison to cells of the same type, i.e. fibroblasts, not having undergone the treatment.

In one embodiment, the iPSCs are characterized by an increase of expression or overexpression of Oct4, Sox-2, Klf-4 and c-Myc.

In one embodiment, the method further comprises the step of isolating said induced pluripotent stem cells by means of a pipetting device, preferably under the microscope. For example, they may be isolated by pipette under light microscope, and may then be recultured in the same or other suitable iPSC medium.

In one embodiment, the fibroblast cells in step a) are mammalian cells, preferably from Primates, more preferably from humans; or they are rodent cells, more preferably from mouse.

In a further aspect, the present invention also relates to an induced pluripotent stem cell or a culture of induced pluripotent stem cells generated by the method according to the present invention, said stem cell(s) being capable of differentiating into different types of cells such as neural and epithelial cells. Different markers can be used to characterize these cells and their origin: desmin, α-SMA, vimentin (mesoderm); AFP (endoderm); GFAP and βIII-tubulin (ectoderm). In cardiomyocyte- or neuron-specific media, cardiomyoctes or neuron cells were obtained, respectively. These cells may be characterized with specific markers such as MEF2C, MYHCB, MYL2A, TnTc and NKX2.5 for cardiomyocytes and AADC, DAT, MAP-2, Chat, GFAP and LMXIB for neurons. Hence, the iPS cells can be differentiated in different types of cells and can be characterized as described above.

The present invention also relates to a differentiated cell derived from an induced pluripotent stem cell or a culture of induced pluripotent stem cells according to the present invention.

The present invention also relates to a tissue of differentiated cells or an organ of differentiated cells derived from induced pluripotent stem cell or a culture of induced pluripotent stem cells according to the present invention.

The present invention also relates to the induced pluripotent stem cell or culture according to the present invention for use in a method of tissue engineering, transplantation, tissue reconstruction, cell therapy procedures, in particular autologous cell therapy procedures, surgical procedures and/or cosmetic procedures. The iPSCs according to the present invention can be differentiated to different types of cells, e.g. cardiomyocytes, neurons, insulin-producing beta cells and others, and then used in cellular or tissue replacements as a result of heart disease, neurodegenerative diseases or diabetes, respectively. They can also be used for cosmetics.

In one embodiment, in the use for such method(s), said use comprises the administration of such induced pluripotent stem cell or differentiated cells derived therefrom to a patient in need thereof.

The present invention also relates to the use of a pluripotent stem cell according to the present invention for the manufacture of a medicament for a method of tissue engineering, transplantation, tissue reconstruction, cell therapy procedures, in particular autologous cell therapy procedures, surgical procedures, and/or cosmetic procedures.

The present invention also relates to a method of tissue engineering, transplantation, tissue reconstruction, cell therapy procedures, surgery or cosmetic treatment, comprising the steps:
generating pluripotent stem cells according to the present invention by a method in accordance with the present invention, and differentiating them into a desired cell type,
applying/administering such differentiated cells to a patient in need thereof. In one embodiment, differentiated specialized cells can be obtained by growing the iPSCs in cell-specific media to replace injured or non-functional cells, e.g. by injecting them into the respective organ where treatment is intended.

Cell-specific media for differentiation of iPSCs are known to a person skilled in the art and are also commercially available from a number of commercial manufacturers, such as e.g. Cell Applications, Inc., San Diego, USA, and others.

In one embodiment, the method according to the present invention is a cosmetic method or a medical treatment method.

Fibroblast cells (NBF-6 and HSFN1) were grown in SFM containing of IL-6 (35 ng/mL), and were frozen/thawed twice, and then were transferred to low attachment plates and were grown in iPSCs medium. Picked colonies were expanded on feeder cells wherein they formed typical iPSC clones, which were named NBF6-IL6-iPSC and HFSN1-IL6-iPSC (FIG. 1A).

Figure 1:
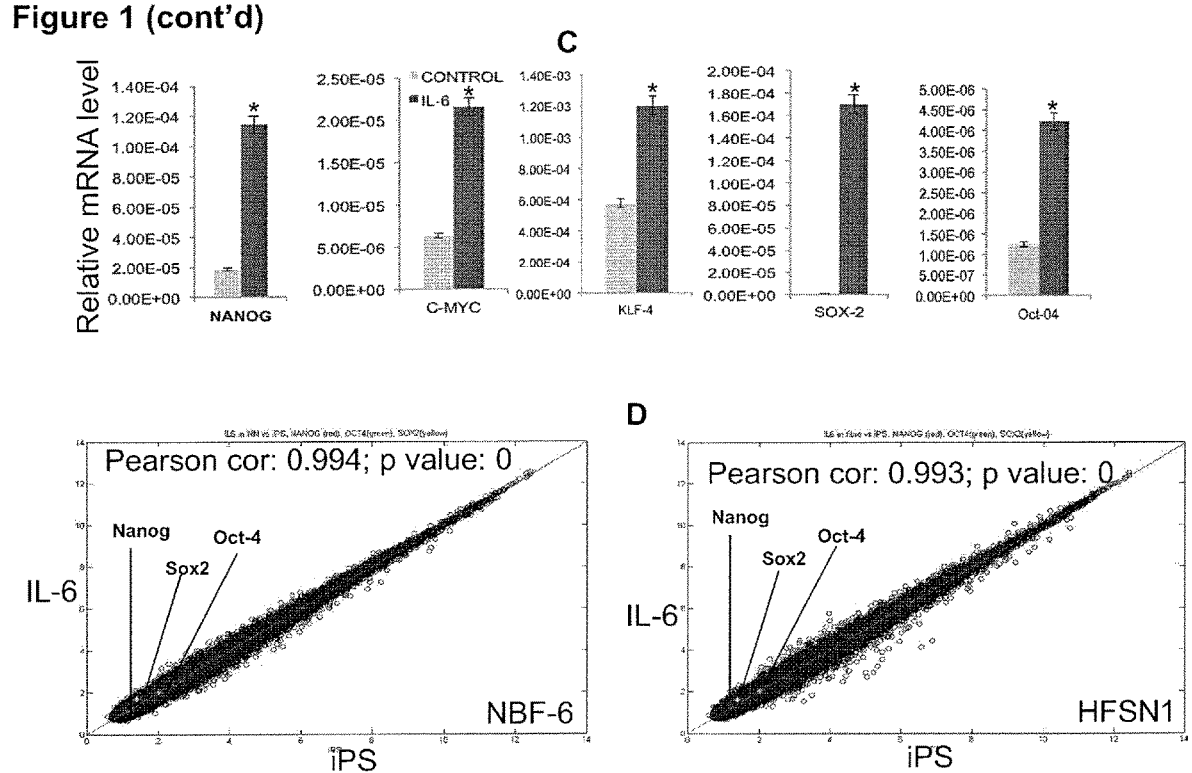
FIG. 1A is a photograph of the typical iPSC clones from NBF6-IL6-iPSC and HFSN1-IL6-iPSC (FIG. 1A), the immunoblotting analysis (FIG. 1B), the expression of the 5 pluripotency markers (i.e. OCT4, KLF4, SOX2, C-MYC and NANOG.
(FIG. 1C), DNA microarray analyses (FIG. 1D) and principal components analysis (FIG. 1E).
Figure 1:
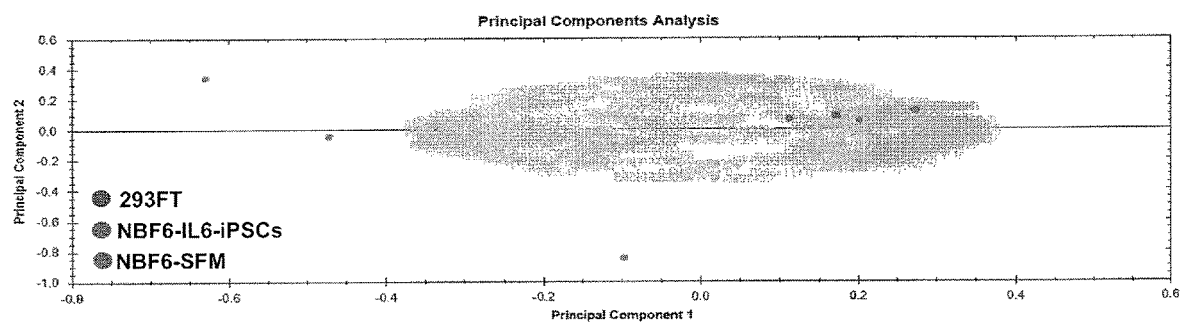

To confirm the iPSC nature of these cells, the inventors first assessed the expression of some stem cell markers and showed that, like embryonic stem cells 293FT, NBF6-IL6-iPSCs exhibited stem cells features ($CD44^{high}/CD24^{low}/ALDH^{high}$) (FIG. 1B). On the other hand, breast stromal fibroblasts (NBF82), luminal (LUM16), myoepithelial (MYO) and SFM (without interleukin-6)-treated NBF-6 cells were ($CD44^{low}/CD24^{high}/ALDH^{low}$) (FIG. 1B). Importantly, IL6-iPSCs as well as 293FT cells, but not the other cells, were positive for the 4 Yamanaka pluripotency transcription factors Oct4, Klf4, Sox2 and c-Myc, in addition to Nanog and BMI-1 (FIG. 1B).

FIG. 1C is the result of quantitative RT-PCR. IL6-iPSCs and 293FT cells, but not the other cells, expressed very low levels of the p16 and p53 tumor suppressor proteins. The increase in the expression of the 4 pluripotency markers was also confirmed at the mRNA level by quantitative RT-PCR (qRT-PCR).

FIG. 1D shows DNA microarray analyses, which demonstrate highly similar transcriptome profile between IL-6 generated iPSCc (NBF6-IL6-iPSCc and HFSN1-IL6-iPSCs) and ATCC-iPSC or 293FT embryonic stem cells.

Likewise, FIG. 1E shows that principal components analysis showed highly similar proteome profile between 293FT cells and NBF6-IL-6.iPSCs, but not their corresponding control cells.

FIG. 2A shows the telomerase activity of NBF6-IL6-iPSCc and HFSN1-IL6-iPSCs cells. The telomerase activity was assessed by the TeloTAGGG Telomerase PCR ELISA assay, and showed that NBF6-IL6-iPSCc and HFSN1-IL6-iPSCs cells have significantly higher telomerase activity as compared to their respective control cells (FIG. 2A).

FIG. 2B shows that NBF6-IL6-iPSCs exhibited exponential growth for 2 months.

Figure 3:
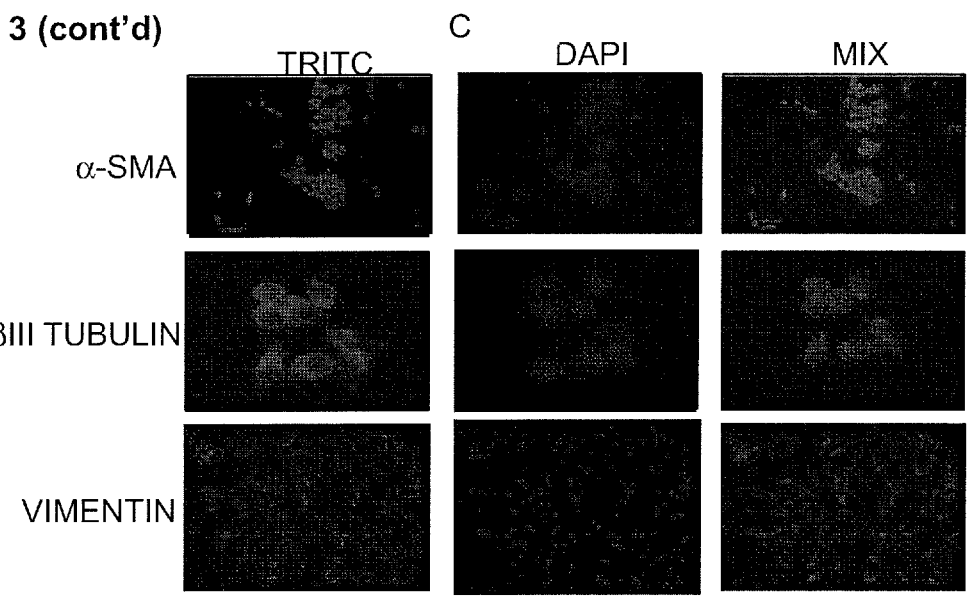

FIG. 3A shows the embryoid body formation and in vitro Differentiation of IL-6-generated iPSCs.

FIG. 3A shows the generation of cells with different shapes, such as neuronal and epithelial.

FIGS. 3B and 3C are graphs of immunofluorescence test and have shown the presence of different types of cells, positive for desmin, α-SMA, vimentin (mesoderm); AFP (endoderm); GFAP and PIII-tubulin (ectoderm).

Figure 4:
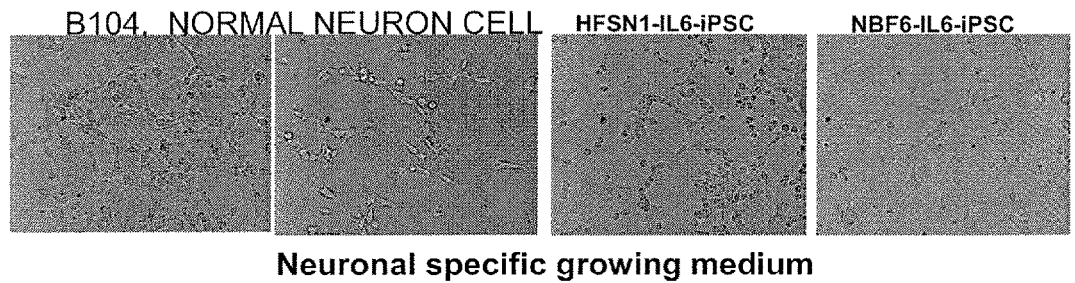
Figure 4:
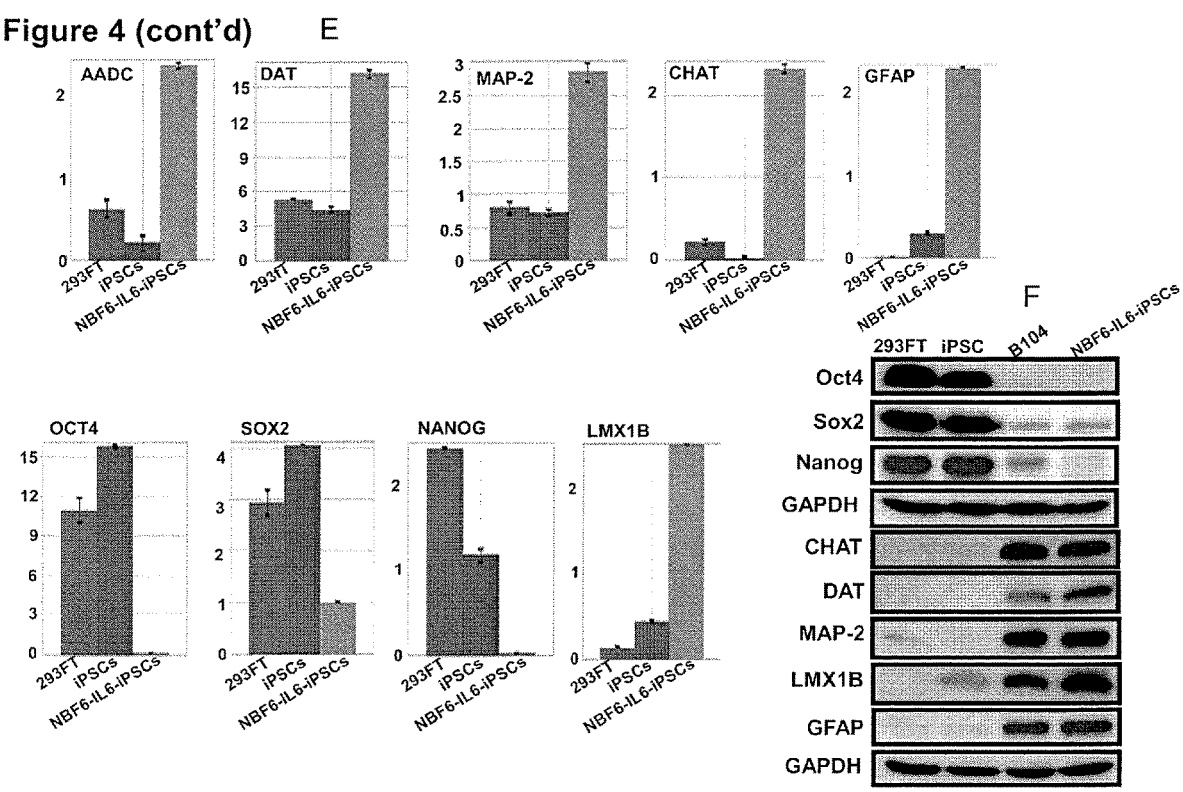

Desmin is a muscle-specific type III intermediate filament protein encoded by the DES gene AFP: Alfa-FetoProtein GFAP: Glial Fibrillary Acidic Protein is expressed by numerous cell types of the central nervous system DAPI=4', 6-Diamidino-2-phenylindole TRITC=tetramethyl rhodamine MIX=Both dyes together FIG. 4A shows cells with some cardiomyocyte structures.

FIGS. 4B and 4C are results of using qRT-PCR and immunoblotting, which shows that cells that were derived from the differentiation of NBF6-IL6-iPSCs and were grown in cardiomyocyte medium expressed high level of several markers of this type of cells, such as MEF2C, MYHCB, MYL2A, TnTc and NKX2.5. On the other hand, the levels of the pluripotency markers, Nanog, Sox2 and Oct4 were reduced in these cells as compared to the original ones or 293FT (FIGS. 4B and 4C).

FIG. 4D are photographs showing cells that were derived from the differentiation of NBF6-IL6-iPSCs and were grown in neuronal medium showed some neuronal structures similar to B104 neuronal cells.

FIGS. 4E and 4F are graphs showing that differentiated NBF6-IL6-iPSCs cells that were grown in neuronal specific medium expressed high level of several markers of this type of cells, such as AADC, DAT, MAP-2, Chat, GFAP and LMX1B. Several proteins were similarly expressed in the neuronal cells B104 and NBF-IL-6-iPSCs (FIG. 4F).

FIGS. 4E and 4F also show that the levels of the pluripotency markers, Nanog, Sox2 and Oct4 were severely reduced in differentiated NBF6-IL-6-iPSC cells as compared to the original ones or 293FT. This indicates that IL-6-generated iPS cells can be differentiated into different types of cells in vitro.

FIG. 5 are photographs showing IL-6-generated iPSCs formed teratoma in nude mice. To test the pluripotency of NBF6-IL6-iPSCs in vivo we transplanted these cells subcutaneously into dorsal flanks of nude mice. Tumors were formed 8 weeks post-injection, and then were excised and were subjected to histological examination, which showed that tumors contain various tissues, such as gut-like epithelium (endoderm), muscle (mesoderm) and epidermis (ectoderm).

DETAILED DESCRIPTION OF THE INVENTION

The present invention successfully provides vector-free IL-6-dependent methods for generating induced pluripotent stem cells from fibroblast cells, such as human and mouse fibroblasts cells.

As used herein, a "stem cell" is a pluripotent cell which possess two properties: 1. The ability of self-renewal; 2. The capacity to differentiate into more than one type of specialized cell types.

As used herein, the term "serum free medium" is a medium which does not include serum or has a concentration of serum equal to or lower than 1% (vol/vol). The term "serum-free" as used herein, is meant to refer to a medium that contains substantially no serum or, at a maximum, 0%-1% (vol/vol) serum, preferably ≤0.2% (vol/vol) serum, wherein, preferably, the serum is fetal bovine serum (FBS). In one embodiment, a "serum-free" medium, as used herein, contains about 0.2% fetal bovine serum.

In one embodiment, a serum-free medium (SFM) is "serum-free" in the sense that it contains substantially no serum or, at a maximum, 0%-1% (vol/vol) serum, preferably ≥0.2% (vol/vol) serum, or such "serum-free medium" is a medium that has only been supplemented, at a maximum, with 0%-1% (vol/vol) serum, preferably 0.2% (vol/vol), or less, serum, preferably with about 0.2% (vol/vol) or less fetal bovine serum (FBS). In one embodiment, a serum-free medium (SFM) comprises or is a 1:1-mixture (vol/vol) of M199 medium and F12 medium, supplemented with 0%-1% (vol/vol) serum, preferably ≥0.2% (vol/vol) serum, preferably fetal bovine serum (FBS), preferably about 0.2% (vol/vol) FBS, and further supplemented with 0.1%-2% (vol/vol) of an antibiotic-antimycotic solution, said antibiotic/antimycotic solution comprising 10000 units/ml penicillin, 10000 sg/ml streptomycin and 25 µg/ml amphotericin B preferably 1% of said antibiotic/antimycotic solutions. Such serum-free medium (SFM) may or may not additionally contain interleukin-6. It does contain interleukin-6 in those embodiments, wherein such serum-free medium is used for the treatment of fibroblast cells. However, it may also be that such serum-free medium does not contain interleukin-6, and in those cases, such serum-free medium is used as a control. For example a serum-free medium that does not contain interleukin-6 is herein also sometimes abbreviated as "SFM" or "SFM-". Where such serum-free medium does additionally contain interleukin-6, this is herein also sometimes abbreviated as "SFM-IL6" or "simply" IL-6.

The term " . . . being supplemented with x % serum" is meant to refer to a scenario wherein the mixture or medium is supplemented with a maximum of x % serum. In one embodiment, such term may also mean that the medium or mixture has not been actively and deliberately supplemented with any serum at all and therefore contains substantially no serum.

In one embodiment the phrase the " . . . medium comprises a . . . mixture, supplemented with . . . " is meant to be understood that the medium "is a . . . mixture supplemented with . . . ".

In one embodiment, the method for generating induced pluripotent stem cells (iPSCs) is an in-vitro method.

As used herein, "stemness" represents the properties of stem cells.

As used herein, the term "patient" represents a human being, or a non-human animal, e.g. a non-human mammal, like a dog, a cat, a rat, a monkey or livestock animals, such as cow, pig, sheep or horse.

As used herein, E-cadherin is a known member of the cadherin family. In adult tissues, E-cadherin is expressed in epithelial tissues. In stem cells, the level of E-cadherin is reduced in comparison to differentiated cells.

As used herein, N-cadherin is a protein that in humans is encoded by the CDH2 gene. N-cadherin is a transmembrane protein expressed in multiple tissues and functions to mediate cell-cell adhesion. In stem cells, the level of N-cadherin is increased in comparison to differentiated cells.

As used herein, the term "differentiation" refers to the process where a cell changes from one cell type to another. A cell that can differentiate into all cell types of the adult organism is known as pluripotent. More specifically, pluripotent stem cells can give rise to cells of all three primitive germ layers upon differentiation. Pluripotent stem cells undergo further specialization into multipotent progenitor cells that then give rise to functional cells.

As used herein, Interleukins are a group of cytokines (secreted proteins and signal molecules) that were first seen to be expressed by white blood cells (leukocytes).

IL-6 is a multifunctional cytokine that plays a key role in both innate and acquired immune responses, hematopoiesis, inflammation as well as in the regulation of growth and differentiation of cancer cells. Interleukin-6 (IL-6) is among those soluble factors that are secreted from both cancer cells and stromal fibroblasts.

In one embodiment, human IL-6 has the amino acid sequence

```
MNSFSTSAFG PVAFSLGLLL VLPAAFPAPV PPGEDSKDVA

APHRQPLTSS ERIDKQIRYI LDGISALRKE TCNKSNMCES

SKEALAENNL NLPKMAEKDG CFQSGFNEET CLVKIITGLL

EFEVYLEYLQ NRFESSEEQA RAVQMSTKVL IQFLQKKAKN

LDAITTPDPT TNASLLTKLQ AQNQWLQDMT THLILRSFKE

FLQSSLRALR QM.
```

Human IL-6 Recombinant protein (hBA-184) (SantaCruzBiotechnology, Inc.).

As used herein, the term "isolated" refers to a cell, such as an epithelial cell, a stem cell or population of daughter stem cells in a non-naturally occurring state outside of the body (e.g. isolated from the body or a biological sample from the body).

As used herein, the term "autologous" as used herein, refers to cells derived from the same subject. In contrast, "heterologous" refers to cells derived from a different subject.

Throughout this application, various media are mentioned and described as being used. For example, the media M199, F12 and DMEM are repeatedly mentioned as being components of the media used in the method according to the present invention. M199 is a tissue culture medium well known (see original publication by Morgan et al., Proc. Soc. Exp. Biol. Med. 73, 1 (1950)), and includes Earle's salts, L-glutamine and sodium bicarbonate. It is commercially available from various manufacturers, such as Sigma Aldrich, Thermo Fischer and others. F12 medium is another medium that is well known and used in cell culture and is also commercially available from various manufacturers, including Sigma Aldrich, Gibco, Thermo Fischer, Lonza and others. DMEM is Dulbecco's modified Eagle's medium and is also available from a number of manufacturers, including Sigma Aldrich and others. B27 is a medium supplement that is well known and that is commercially available from various manufacturers.

In accordance with embodiments of the present invention, there is provided a method for generating induced pluripotent stem cells comprising the step:

a) providing isolated fibroblast cells and treating such fibroblast cells with interleukin-6 in a growth medium.

The inventors have surprisingly found that a treatment of such fibroblast cells with interleukin-6 results in a switch and dedifferentiation of the fibroblast cells to generate induced pluripotent stem cells. Hence the present invention also relates to the use of interleukin-6 for generating induced pluripotent stem cells, wherein said use comprises treating fibroblast cells with interleukin-6. This is a simple and easy method to perform and results in the formation of pluripotent stem cells. In one embodiment, the growth medium for the treatment of fibroblast cells with IL-6 is serum-free medium as described above. In one embodiment, in step b), cells are first grown in fibroblast growth medium (FGM), as described above; preferably they are grown until they reach 70%-80% confluency. Thereafter they are treated with interleukin-6 by exposing them to a serum-free medium, as defined above, which additionally comprises interleukin-6 (IL-6). In one embodiment such treatment or exposure occurs for a time period, as defined above and also below, e.g. in the range of from 12 hours to 48 hours. After treatment, the thus treated cells are grown in fibroblast growth medium (FGM) again, preferably until they reach confluency.

In one embodiment, the method further comprises the step: c) performing 1-5, preferably 2-3, more preferably 2 cycles of freezing/thawing, and then growing cells until the formation of cellular floating aggregates.

Once the growth has reached that stage, in one embodiment, the method further comprises a step d) transferring cells to an iPSC growth medium and growing them further until the formation of colonies of cells and expanding further such colonies on feeder cells to result in induced pluripotent stem cells (iPSCs). In one embodiment, the iPSCs produced by the transfer and growth step d) form embryoid bodies which embryoid bodies have a size in the range of from 50 to 300 microns.

In accordance with embodiments of the present invention, the treatment of fibroblast cells with interleukin-6 in step a) lasts 2-100 hours, preferably in the range of from 12 hours to 72 hours, more preferably in the range of from 12 hours to 48 hours, even more preferably in the range of from 12 hours to 36 hours, even more preferably in the range of 12 hours to 30 hours, even more preferably in the range of from 20 hours to 28 hours, even more preferably 24 hours.

In one embodiment, the method further comprises the step: e) characterizing molecular and cellular characteristics of the formed iPSCs.

The interleukin-6 that may be used in accordance with embodiments of the present invention may be interleukin-6 that has been isolated from its natural environment, e.g. blood or cell culture, or it may be recombinant interleukin-6.

In one preferred embodiment, interleukin-6 is human interleukin-6, wherein, preferably, said interleukin is recombinant human interleukin-6.

In accordance with embodiments of the present invention, said interleukin-6 is used in step b) in SFM at a concentration in the range of from 1 ng/ml to 100 ng/ml, preferably, 10 ng/ml to 50 ng/ml, more preferably, 20 ng/ml to 40 ng/ml, even more preferably about 35 ng/ml.

In one embodiment, the growing of said cells in step d) occurs in an environment that favors suspension cell culture, e.g. low attachment plates.

In one embodiment, the induced pluripotent stem cells are produced by the performance of steps a-d) and are characterized by the up-regulation of one or several, preferably all of the following: CD44, ALDH, Oct3/4, Sox2, Klf4, c-Myc, Nanog, BMI-1 and reduced or absence of expression of CD24 as well as p16 and p53 in comparison to cells of the same type, i.e. e.g. breast stromal fibroblasts (NBF82), luminal (LUM16), myoepithelial (MYO) and/or SFM-treated NBF-6 cells, not having undergone the treatment with interleukin-6.

The present invention as described above allows reprogramming up to 1.3% of the treated cells, which is considerably better than any of the previously reported methods. The method according to the present invention is a vector-free IL-6-dependent method.

In one embodiment, the method of generating pluripotent stem cells according to the present invention does not involve an ectopic expression of genes, e.g. an ectopic expression of KLF4, OCT3/4, SOX2 and/or c-MYC, and or it does not involve the treatment of the cells with any interleukin other than interleukin-6 and also not any treatment with vitamin C and also not any transfection of microRNA into said cells.

In a further aspect, the present invention also relates to an induced pluripotent stem cell or a culture of induced pluripotent stem cells generated by the method according to the present invention. Such stem cell(s) is (are) capable of differentiating into various different types of cells as for example shown in FIG. 3. When differentiated and grown in cell-specific media, they show features of these specific differentiated cells, e.g. myocytes or neuronal cells and may be characterized as for example shown in FIG. 4.

In a further aspect, such induced pluripotent stem cells may also be differentiated again, and the present invention also relates to a differentiated cell derived from an induced pluripotent stem cell or a culture of induced pluripotent stem cells according to the present invention.

The present invention also relates to a tissue of differentiated cells or an organ of differentiated cells derived from induced pluripotent stem cell produced or generated according to the present invention.

The present invention also relates to a culture of induced pluripotent stem cells produced or generated according to the present invention.

The present invention also relates to the induced pluripotent stem cell or culture according to the present invention for use in a method of tissue engineering, transplantation, tissue reconstruction, cell therapy procedures, in particular autologous cell therapy procedures, wherein said use comprises the administration of such induced pluripotent stem cell or differentiated cells derived therefrom to a patient in need thereof.

The present invention also relates to the use of a pluripotent stem cell according to the present invention for the manufacture of a medicament for a method of tissue engineering, transplantation, tissue reconstruction, cell therapy procedures, in particular autologous cell therapy procedures.

The present invention also relates to a method of tissue engineering, transplantation, tissue reconstruction, cell therapy procedures, in particular autologous cell therapy procedures,
generating pluripotent stem cells according to the present invention by a method in accordance with the present invention, and differentiating them into a desired cell type,
applying/administering such differentiated cells to a patient in need thereof. For example, such differentiated cells may be used for autologous therapeutic replacement or cosmetic intervention.

In one embodiment, the method of tissue engineering according to the present invention is a cosmetic method. In another embodiment, the method according to the present invention is a medical treatment method, preferably, autologous cell therapy method.

The invention is now further described by reference to the following examples which are given to illustrate not to limit the present invention.

Examples

Materials and Methods

Fibroblast cells from breast (NBF-6) and skin (HSFN1) were treated with recombinant human interleukin-6 (IL-6) in serum-free medium for 24 hours. Serum-free medium (SFM), breast stromal fibroblasts (NBF82), luminal (LUM16), myoepithelial (MYO) and SFM-treated NBF-6 cells were used as controls.
Growth Media for Fibroblast Luminal and Myoepithelial Cells:
Fibroblast Cells
1:1 mixture (vol/vol) of M199 medium and F12 medium, supplemented with 1%-20% (vol/vol) fetal bovine serum (FBS), preferably 20% (vol/vol) FBS and 0.1%-2% (vol/vol) of an antibiotic-antimycotic solution as defined above (100× mixture of different antibiotics and antimycotics solution as defined above, purchased from Gibco cat #15240-062) preferably 1% of said antibiotic/antimycotic solution.
Luminal Cells
1:1 mixture (vol/vol) of DMEM medium and F12 medium supplemented with 1%-10% (vol/vol) fetal bovine serum (FBS), preferably 2% (vol/vol), 0.1%-2% (vol/vol) of an antibiotic-antimycotic solution as defined above (100×mixture of different antibiotics and antimycotics solution as defined above, purchased from Gibco cat #15240-062), preferably 1% (vol/vol), HuMEC Supplementary kit (purchased from gipco Cat #12754-016), and bovine pituitary extract (5 µg/ml).
Myoepithelial Cells
The composition of this medium is as described in Table 2:

| Supplement | Final Conc |
| --- | --- |
| 500 mL of M199/F12 (1:1) | |
| 2.5 mL Insulin-Transferrin-Selenium (ITS) from GIBCO | 10 µg/mL |
| 2.5 mg Insulin (Powder) | |
| 100 µL (0.1 µg/µL EGF) | 20 ng/mL |
| 125 µL HC (1 mg/mL) | 250 ng/mL |
| 0.5 mL O-Phosphoethanolamine | $10^{-4}$M |
| 0.5 mL Ethanolamine | $10^{-4}$M |
| 44 µL *PGE1 | 8.8 µg/mL |

Results
IL-6 Induces Pluripotency in Fibroblast Cells
Fibroblast cells (NBF-6 and HSFN1) were grown in SFM containing or not containing IL-6 (35 ng/mL), and were frozen/thawed twice, and then were transferred to low attachment plates and were grown in iPSCs medium. Picked colonies were expanded on feeder cells wherein they formed typical iPSC clones, which were named NBF6-IL6-iPSC and HFSN1-IL6-iPSC (FIG. 1A).

To confirm the iPSC nature of these cells, the inventors first assessed the expression of some stem cell markers and have shown that, like embryonic stem cells 293FT, NBF6-IL6-iPSCs exhibited stem cells features ($CD44^{high}$/$CD24^{low}$/$ALDH^{high}$) (FIG. 1B).

On the other hand, breast stromal fibroblasts (NBF82), luminal (LUM16), myoepithelial (MYO) and SFM-treated NBF-6 cells were ($CD44^{low}/CD24^{high}/ALDH^{low}$) (FIG. 1B). Importantly, IL6-iPSCs as well as 293FT cells, but not the other cells, were positive for the 4 Yamanaka pluripotency transcription factors Oct4, Klf4, Sox2 and c-Myc, in addition to Nanog and BMI-1 (FIG. 1B). On the other hand, IL6-iPSCs and 293FT cells, but not the other cells, expressed very low levels of the p16 and p53 tumor suppressor proteins. The increase in the expression of the 4 pluripotency markers was also confirmed at the mRNA level by quantitative RT-PCR (qRT-PCR) (FIG. 1C).

RNA Purification and qRT-PCR

Total RNA was purified using the TRI reagent (Sigma) according to the manufacturer's instructions, and was treated with RNase-free DNase before cDNA synthesis using the RT-PCR Kit (Clontech, USA). For quantitative RT-PCR (qRT-PCR), the $RT^2$ Real-Time SYBR Green qPCR mastermix (Roche, Germany) was used and the amplifications were performed utilizing the light cycler 480 (Roche, germany). The melting-curve data were collected to check PCR specificity, and the amount of PCR products was measured by threshold cycle (Ct) values and the relative ratio of specific genes to GAPDH for each sample was then calculated.

DNA microarray analyses demonstrated highly similar transcriptome profile between IL-6 generated iPSCs (NBF6-IL6-iPSCs and HFSN1-IL6-iPSCs) and ATCC-iPSC or 293FT embryonic stem cells (FIG. 1D). Likewise, principal components analysis showed highly similar proteome profile between 293FT cells and NBF6-IL-6.iPSCs, but not their corresponding control cells (FIG. 1E).

Affymetrix Exon Array Experiments

The GeneChip® Human Exon 1.0 ST Arrays (HE 1.0 STAs) contains ~5.4 million, 5-μm features (probes) grouped into 1.4 million probesets, interrogating over 1 million exon clusters using approximately four probes per exon and roughly 40 probes per gene. This high density exonic approach enables gene and exon level expression analyses and facilitates detection of the most complex transcriptomic changes due to exon skipping, intron retention, alternative splicing and alternative promoter usages. To be able to examine expression changes at gene level, we utilized HE 1.0 STAs in our research. First, total RNA was extracted using standard protocols. The total RNA quantity and quality was determined by using Nanodrop ND-1000 UV-spectrophotometer (NanoDrop Technologies) and Agilent 2100 Bioanalyzer (Agilent Technologies), respectively. All HE 1.0 STAs related procedures were performed according to Affymetrix's protocols and guidelines using whole transcript sense target labeling assay. Briefly total RNA was spiked in with Poly-A RNA controls provided by Affymetrix and rRNA reduction was performed using RiboMinus Human Transcriptome Isolation Kit (Life Sciences Corp., Grand Island, N.Y., USA). First cycle, first and second cDNA synthesis, and in vitro transcription were performed on the extracted total RNA. Then the freshly synthesized cRNA was purified and used for $2^{nd}$ cycle $1^{st}$ strand cDNA synthesis which was followed by cRNA hydrolysis and sense strand DNA cleanup. The fragmentation, terminal labeling, and overnight hybridizations were done according to the standard Affymetrix protocols as described in the assay manual. The HE 1.0 STAs were washed in the Affymetrix's Fluidics Station 450 and scanned on the GeneChip scanner 3000 (Affymetrix Inc.). Exon Array Computational Tool (Affymetrix Inc.) was used to perform quality assessment and initial analysis.

Global Gene Expression Comparison

The global gene expression patterns were compared between IL-6 generated iPSCs (NBF6-IL6-iPSCs and HFSN1-IL6-iPSCs) and ATCC-iPSC. Correlations between continuous data were estimated by Pearson's correlation coefficient (r) and associated p-values were computed by transforming the correlation to create a t statistic. All statistical analyses were performed with the MATLAB software packages (Mathworks, Natick, Mass., USA), PARTEK Genomics Suite (Partek Inc., St. Lois, Mo., USA), and SAS 9.4 (Statistical Analysis System, SAS Institute Inc., Cary, N.C., USA). A p-value of <0.05 was considered significant.

Sample Preparation for Label-Free Protein In-Solution Digestion

Whole cell lysate samples were subjected to proteome analysis. For each sample a total of 100 μg protein was subjected to in-solution tryptic digestion as previously described. Briefly Proteins were denatured in 0.1% RapiGest SF at 80° C. for 15 minutes, reduced in 10 mM Dithiothreitol (DTT) at 60° C. for 30 min, and alkylated in 10 mM Iodoacetamide (IAA) (1.0 μL IAA/10 μL) in the dark for 40 min at room temperature. Samples were trypsin-digested overnight at 37° C. and were diluted with aqueous 0.1% formic acid prior to LC/MS analysis.

Protein Identification by LC-$MS^E$ SynaptG2 Platform

Label-free quantitative 1-dimensional Nano Acquity liquid chromatography tandem mass spectrometry on Synapt G2 (Waters, Manchester, UK) was used to generate expression protein profiles between the sample groups. The detector of the instrument was set up using 2 ng/μL leucine Enkephalin. A separate infusion of 500 fmol [Glu] 1-fibrinopeptide B was used for mass (m/z) calibration on the Mass Lynx IntelliStart (Waters, Manchester, UK). All analyses were performed on Triazaic Nano source, and ionization in the positive ion mobility mode nanoESI (Waters, Manchester, UK). Data-independent acquisition (MSE)/iron mobility separation was performed and data acquired over a range of m/z 50-2000 Da using the Mass Lynx programs (version. 4.1, SCN833, Waters, Manchester, UK). All samples were analyzed in triplicate runs and automated data processing and database search was performed using the Uniprot Human specific protein sequence database on Progenesis QI for protein identification platform (Waters, UK and Nonlinear Dynamics, Newcastle, UK).

IL-6-Generated Human iPSCs Exhibit High Telomerase Activity and Exponential Growth Next, telomerase activity was assessed by the TeloTAGGG Telomerase PCR ELISA assay, and showed that NBF6-IL6-iPSCs and HFSN1-IL6-iPSCs cells have significantly higher telomerase activity as compared to their respective control cells (FIG. 2A). Furthermore, NBF6-IL6-iPSCs exhibited exponential growth for 2 months (FIG. 2B).

Telomerase Activity Assay

Telomerase activity assay was performed using TeloTAGGG Telomerase PCR ELISA assay (Roche) as instructed by the manufacturer. Briefly, 20 μg of heat- or sham-treated cell extracts were amplified by PCR (94° C. for 30 sec, 50° C. for 30 sec and 72° C. for 90 sec). The PCR products were hybridized to anti-digoxigenin-peroxidase and then ELISA reaction was performed and the OD was measured at 450 nm on a standard ELISA plate-reader (x-Mark, BIO-RAD).

Heat at 85 C for 10 min serves the purpose to destroy telomerase activity and is used as negative control.

Embryoid Body Formation and In Vitro Differentiation of IL-6-Generated iPSCs

In order to further characterize the IL-6-generated iPSCs, the inventors investigated their differentiation ability in vitro. To this end, NBF6-IL6-iPSCc cells were cultured in suspension, till embryoid bodies were formed (FIG. 3A), and then were transferred to gelatin-coated plates for in vitro differentiation. FIG. 5A shows the generation of cells with different shapes, such as neuronal and epithelial. Next, the inventors characterized these cells by immunofluorescence and have shown the presence of different types of cells, positive for desmin, α-SMA, vimentin (mesoderm); AFP (endoderm); GFAP and βIII-tubulin (ectoderm) (FIG. 3B).

Embryoid Body-Differentiation

IPS cells were harvested by treating with StemPro Accurase (cell dissociation reagent (gipco), and were transferred to low attachment 6 well plate in the presence of iPSC medium for 5 days. The newly formed embryoid bodies were then transferred to gelatin-coated plate and were cultured in the same medium for 8-10 days. This generated cells with different shapes that were monitored under microscope.

For differentiation into neurons, embryoid bodies were transferred to gelatin-coated plate in the presence of neuron-specific medium as shown in Table 3.

| Component | Final Concentration | Amount (100 mL) |
| --- | --- | --- |
| Neurobasal Medium | 1X | 97 mL |
| GlutaMax | 2 mM | 1 mL |
| B-27 Suplement | 2% | 2 mL |
| Ascorbic acid | 200 uM | 100 uL |

Regarding iPSC differentiation into cardiomyocytes, embryoid bodies were transferred to gelatin-coated plate and were cultured following the PSC Cardiomyocyte Differentiation Kit (gibco cat. #A29212-01) following the instructions of the manufacturer. Cells with cardiomyocyte-like shape appeared after 5 days of incubation.

FIG. 4A shows cells with some cardiomyocyte structures. Using qRT-PCR and immunoblotting, it has been shown that cells that were derived from the differentiation of NBF6-IL6-iPSCs and were grown in cardiomiocyte medium expressed high level of several markers of this type of cells, such as MEF2C, MYHCB, MYL2A, TnTc and NKX2.5 (FIGS. 4B and 4C). On the other hand, the levels of the pluripotency markers, Nanog, Sox2 and Oct4 were reduced in these cells as compared to the original ones or 293FT (FIGS. 4B and 4C). Similarly, cells that were derived from the differentiation of NBF6-IL6-iPSCs and were grown in neuronal medium showed some neuronal structures similar to B104 neuronal cells (FIG. 4D), and also expressed high level of several markers of this type of cells, such as AADC, DAT, MAP-2, Chat, GFAP and LMXIB (FIGS. 4E and 4F). Several proteins were similarly expressed in the neuronal cells B104 and NBF6-IL-6-iPSCs (FIG. 4F). On the other hand, the levels of the pluripotency markers, Nanog, Sox2 and Oct4 were severely reduced in NBF6-IL-6-iPSC cells as compared to the original ones or 293FT (FIGS. 4F and 4F). This indicates that IL-6-generated iPS cells can be differentiated into different types of cells in vitro.

Teratoma Formation from IL-6-Generated iPSCs

To test the pluripotency of NBF6-IL6-iPSCs in vivo we transplanted these cells subcutaneously into dorsal flanks of nude mice. Tumors were formed 8 weeks post-injection, and then were excised and were subjected to histological examination, which showed that tumors contain various tissues, such as gut-like epithelium (endoderm), muscle (mesoderm) and epidermis (ectoderm) (FIG. 5).

iPS cells were dissociated by cell dissociation reagent (gipco), centrifuged, and the pellet was resuspended in iPSC growing medium. 250 000 cells were injected subcutaneously to dorsal flanks of nude mice. 8 weeks post-injection, tumors were excised and paraffin-embedded tissues were sliced and stained with hematoxylin and eosin, and then were subjected to histological examination.

CONCLUSION

Together, these results indicate that IL-6 treatment associated with 2 freezing/thawing cycles is capable of dedifferentiating fibroblast cells into pluripotent stem cells.

The features of the present invention discloses in the specification, the claims, and/or in the accompanying drawings may, both separately and in any combination thereof, be material for realizing the invention in various forms thereof. Further modifications of the preferred embodiments are possible without leaving the scope of the invention which is solely defined by the claims.

REFERENCES

Akira et al., Molecular cloning of APRF, a novel IFN-stimulated gene factor 3 p91-related transcription factor involved in the gp130-mediated signaling pathway. Cell 1994, 77, 63-71.

Brady et al., Early role for IL-6 signalling during generation of induced pluripotent stem cells revealed by heterokaryon RNA-Seq. Nat Cell Biol 2013, 15, 1244-1252.

Chen et al., H3K9 methylation is a barrier during somatic cell reprogramming into iPSCs. Nat Genet 2013, 45, 34-42.

Dethlefsen et al., The role of intratumoral and systemic IL-6 in breast cancer. Breast Cancer Res Treat 2013, 138, 657-664.

Esteban et al., Vitamin C improves the quality of somatic cell reprogramming. Nat Genet 2012, 44, 366-367.

Esteban et al., Vitamin C enhances the generation of mouse and human induced pluripotent stem cells. Cell stem cell 2010, 6, 71-79.

Gao et al., Mutations in the EGFR kinase domain mediate STAT3 activation via IL-6 production in human lung adenocarcinomas. J Clin Invest 2007, 117, 3846-3856.

Knupfer et al., Significance of interleukin-6 (IL-6) in breast cancer (review). Breast Cancer Res Treat 2007, 102, 129-135.

Li et al., A mesenchymal-to-epithelial transition initiates and is required for the nuclear reprogramming of mouse fibroblasts. Cell stem cell 2010, 7, 51-63.

Lieblein et al., STAT3 can be activated through paracrine signaling in breast epithelial cells. BMC cancer 2008, 8, 302.

Liu et al., Sequential introduction of reprogramming factors reveals a time-sensitive requirement for individual factors and a sequential EMT-MET mechanism for optimal reprogramming. Nat Cell Biol 2013, 15, 829-838.

Miyoshi et al., Reprogramming of mouse and human cells to pluripotency using mature microRNAs. Cell stem cell 2011, 8, 633-638.

Raz et al., Essential role of STAT3 for embryonic stem cell pluripotency. Proc Natl Acad Sci USA 1999, 96, 2846-2851.

Samavarchi-Tehrani et al., Functional genomics reveals a BMP-driven mesenchymal-to-epithelial transition in the initiation of somatic cell reprogramming. Cell stem cell 2010, 7, 64-77.

Sriuranpong et al., Epidermal growth factor receptor-independent constitutive activation of STAT3 in head and neck squamous cell carcinoma is mediated by the autocrine/paracrine stimulation of the interleukin 6/gp130 cytokine system. Cancer Res 2003, 63, 2948-2956.

Wang et al., The histone demethylases Jhdm1a/1b enhance somatic cell reprogramming in a vitamin-C-dependent manner. Cell stem cell 2011, 9, 575-587.

The invention claimed is:

1. A method for generating induced pluripotent stem cells (iPSCs) consisting of the steps:
   a) providing isolated fibroblast cells;
   b) growing fibroblast cells obtained in step a) in a fibroblast growth medium (FGM) supplemented with serum, and then treating the fibroblast cells with interleukin-6 (IL-6) in a serum-free medium (SFM) consisting of a 1:1 mixture (v/v) of M199 medium and F12 medium, IL-6, ≤0.2% (v/v) fetal bovine serum, 0.1%-2% (v/v) antibiotic-antimycotic solution containing 10000 units/ml penicillin, 10000 µg/ml streptomycin and 25 µg/ml amphotericin B; and then growing the IL-6 treated fibroblast cells in the FGM supplemented with serum again;
   c) performing 2-5 cycles of freezing the IL-6 treated fibroblast cells obtained in step b) in a freezing medium and subsequently thawing the frozen fibroblast cells, and then growing the thawed fibroblast cells until the formation of cellular floating aggregates; and
   d) transferring the cells obtained in step c) to a growth medium for induced pluripotent stem cells (iPSCs) and growing said cells further until the formation of colonies and expanding further such colonies on feeder cells to result in induced pluripotent stem cells (iPSCs);
   wherein the method does not involve an ectopic expression of genes KLF4, Oct3/4, Sox2 and c-Myc.

2. The method according to claim 1, further comprising the step:

e) characterizing molecular and cellular characteristics of the formed iPSCs.

3. The method according to claim 1, wherein the treatment of step b) lasts for 12 hours to 48 hours.

4. The method according to claim 1, wherein the serum-free medium in step b) consists of a 1:1-mixture (vol/vol) of M199 medium and F12 medium, IL-6, 0.2% (vol/vol) fetal bovine serum, and 0.1%-2% (vol/vol) of an antibiotic-antimycotic solution containing 10000 units/ml penicillin, 10000 μg/ml streptomycin and 25 μg/ml amphotericin B, and wherein the fibroblast growth medium (FGM) in step b) comprises a 1:1-mixture (vol/vol) of M199 medium and F12 medium supplemented with 10%-20% (vol/vol) fetal bovine serum, and further being supplemented with 0.1%-2% (vol/vol) of antibiotic-antimycotic solution, said antibiotic-antimycotic solution comprising 10000 units/ml penicillin, 10000 μg/ml streptomycin and 25 μg/ml amphotericin B.

5. The method according to claim 1, wherein said interleukin-6 is human interleukin-6.

6. The method according to claim 1, wherein said interleukin-6 is used in step b) in the serum-free medium (SFM) at a concentration in the range of from 10 ng/ml to 50 ng/ml.

7. The method according to claim 1, wherein the induced pluripotent stem cells are produced by the performance of step a)-d) and are characterized by higher expression of one or more of the following: CD44, ALDH, Oct3/4, Sox2, KLF4, c-Myc, Nanog, BMI-1; and reduced or absence of expression of CD24 as well as p16 and p53 in comparison to cells of the same type not having undergone the treatment.

8. The method according to claim 1, wherein the fibroblast cells in step a) are mammalian cells from a human or from a rodent.

9. The method according to claim 1, wherein said method is a vector-free method.

10. The method according to claim 1, wherein the fibroblast growth medium (FGM) in step b) consists of a 1:1-mixture (vol/vol) of M199 medium and F12 medium, 1%-20% (vol/vol) fetal bovine serum, and 0.1%-2% (vol/vol) of antibiotic-antimycotic solution containing 10000 units/ml penicillin, 10000 μg/ml streptomycin and 25 μg/ml amphotericin B.

11. A method of tissue engineering, transplantation, tissue reconstruction, or cell therapy, comprising the steps:
generating pluripotent stem cells by a method according to claim 1, and differentiating them into a desired cell type, and
applying/administering such differentiated cells to a patient in need thereof.

12. The method according to claim 11, wherein said method is a cosmetic method or a medical treatment method.

13. A method for generating induced pluripotent stem cells (iPSCs) consisting of the steps:
a) providing isolated fibroblast cells;
b) growing fibroblast cells obtained in step a) in a fibroblast growth medium (FGM) supplemented with serum, and then treating the fibroblast cells with interleukin-6 (IL-6) in a serum-free medium (SFM) consisting of a 1:1 mixture (v/v) of M199 medium and F12 medium, IL-6, 0-1% (v/v) fetal bovine serum, 0.1%-2% (v/v) antibiotic-antimycotic solution containing 10000 units/ml penicillin, 10000 μg/ml streptomycin and 25 μg/ml amphotericin B; and then growing the IL-6 treated fibroblast cells in the FGM supplemented with serum again;
c) performing 2-5 cycles of freezing the IL-6 treated fibroblast cells obtained in step b) in a freezing medium and subsequently thawing the frozen fibroblast cells, and then growing the thawed fibroblast cells until the formation of cellular floating aggregates;
d) transferring the cells obtained in step c) to a growth medium for iPSCs and growing said cells further until the formation of colonies and expanding further such colonies on feeder cells to result in iPSCs; and
e) isolating the iPSCs;
wherein the method does not involve an ectopic expression of genes KLF4, Oct3/4, Sox2 and c-Myc.

14. The method according to claim 13, wherein the serum-free medium in step b) consists of a 1:1-mixture (vol/vol) of M199 medium and F12 medium, IL-6, ≤0.2% (vol/vol) fetal bovine serum, and 0.1%-2% (vol/vol) of an antibiotic-antimycotic solution containing 10000 units/ml penicillin, 10000 g/ml streptomycin and 25 μg/ml amphotericin B.

15. The method according to claim 13, wherein the fibroblast growth medium (FGM) in step b) consists of a 1:1-mixture (vol/vol) of M199 medium and F12 medium, 1%-20% (vol/vol) fetal bovine serum, and 0.1%-2% (vol/vol) of antibiotic-antimycotic solution containing 10000 units/ml penicillin, 10000 μg/ml streptomycin and 25 μg/ml amphotericin B.

16. The method according to claim 13, wherein said interleukin-6 is used in step b) in the serum-free medium (SFM) at a concentration in the range of from 10 ng/ml to 50 ng/ml.

* * * * *

```
                       SEQUENCE LISTING

<160> NUMBER OF SEQ ID NOS: 1

<210> SEQ ID NO 1
<211> LENGTH: 212
<212> TYPE: PRT
<213> ORGANISM: Homo sapiens
<220> FEATURE:
<221> NAME/KEY: MISC_FEATURE
<222> LOCATION: (1)..(212)
<223> OTHER INFORMATION: interleukin-6

<400> SEQUENCE: 1

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210
```